US008105961B2

(12) United States Patent
Curry

(10) Patent No.: US 8,105,961 B2
(45) Date of Patent: Jan. 31, 2012

(54) METHOD AND APPARATUS FOR USING FLEX CIRCUIT TECHNOLOGY TO CREATE A REFERENCE ELECTRODE CHANNEL

(75) Inventor: Kenneth M. Curry, Oceanside, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 288 days.

(21) Appl. No.: 12/537,031

(22) Filed: Aug. 6, 2009

(65) Prior Publication Data

US 2009/0291555 A1 Nov. 26, 2009

Related U.S. Application Data

(62) Division of application No. 11/710,280, filed on Feb. 22, 2007, now Pat. No. 7,586,173.

(60) Provisional application No. 60/777,133, filed on Feb. 27, 2006.

(51) Int. Cl.
*H01L 21/31* (2006.01)
*H01L 21/469* (2006.01)

(52) U.S. Cl. . 438/780; 438/637; 438/686; 257/E21.006; 257/E21.027; 257/E21.058; 257/E21.264; 257/E21.267

(58) Field of Classification Search .......... 438/780, 438/637, 686, 687, 552, 555; 257/E21.006, 257/27, 958, 24, 264, 267

See application file for complete search history.

(56) References Cited

U.S. PATENT DOCUMENTS

| | | | |
|---|---|---|---|
| 4,542,291 A | 9/1985 | Zimmerman |
| 4,549,952 A | 10/1985 | Columbus |
| 4,937,444 A | 6/1990 | Zimmerman |
| 5,423,883 A | 6/1995 | Helland |
| 5,838,546 A | 11/1998 | Miyoshi |
| 5,987,361 A | 11/1999 | Mortimer |
| 6,572,748 B1 | 6/2003 | Hermann et al. |
| 6,833,612 B2 | 12/2004 | Kinsman |
| 6,885,107 B2 | 4/2005 | Kinsman |
| 6,940,141 B2 | 9/2005 | Kinsman |
| 6,956,295 B2 | 10/2005 | Kinsman |
| 6,964,886 B2 | 11/2005 | Kinsman |

(Continued)

FOREIGN PATENT DOCUMENTS

EP  0230645  8/1987

(Continued)

OTHER PUBLICATIONS

International Search Report, PCT US2007/004696, Aug. 29, 2007.

*Primary Examiner* — David Nhu
(74) *Attorney, Agent, or Firm* — Michael Crapenhoft

(57) ABSTRACT

A method of creating a sensor that may include applying a first conductive material on a first portion of a substrate to form a reference electrode and depositing a first mask over the substrate, the first mask having an opening that exposes the reference electrode and a second portion of the substrate. The method may also include depositing a second conductive material into the opening in the first mask, the second conductive material being in direct contact with the reference electrode and depositing a second mask over the second conductive material, the second mask having an opening over the second portion of the substrate, the opening exposing a portion of the second conductive material which forms a working surface to receive a fluid of interest.

13 Claims, 4 Drawing Sheets

U.S. PATENT DOCUMENTS

| | | |
|---|---|---|
| 6,972,423 B2 | 12/2005 | Welland et al. |
| 6,985,764 B2 | 1/2006 | Mason et al. |
| 7,101,472 B2 * | 9/2006 | Dineen et al. .................. 205/792 |
| 7,122,390 B2 | 10/2006 | Kinsman |
| 7,586,173 B2 * | 9/2009 | Curry ............................ 257/499 |
| 2005/0191428 A1 | 9/2005 | Buck |

FOREIGN PATENT DOCUMENTS

| | | |
|---|---|---|
| WO | 8907758 | 8/1989 |
| WO | 2005085826 | 9/2005 |

* cited by examiner

METHOD AND APPARATUS FOR USING FLEX CIRCUIT TECHNOLOGY TO CREATE A REFERENCE ELECTRODE CHANNEL

RELATED APPLICATIONS

The present Application for Patent is a divisional application of U.S. patent application Ser. No. 11/710,280, filed Feb. 22, 2007, now U.S. Pat. No. 7,586,173, entitled "Method and Apparatus for Using Flex Circuit Technology to Create a Reference Electrode Channel," which claims priority to Provisional Application No. 60/777,133, filed Feb. 27, 2006, both of which are assigned to the assignee hereof and the contents of which are hereby expressly incorporated by reference herein.

FIELD OF THE INVENTION

The invention relates generally to flex circuit technology. More specifically, the invention relates to using flex circuit technology to create a reference electrode channel.

BACKGROUND

Flex circuits have been used in the micro-electronics industry for many years. In recent years, flex circuits have been used to design microelectrodes for in vivo applications. One flex circuit design involves a laminate of a conductive foil (e.g., copper) on a flexible dielectric substrate (e.g., polyimide). The flex circuit is formed on the conductive foil using masking and photolithography techniques. Flex circuits are desirable due to their low manufacturing cost, ease in design integration, and flexibility in motion applications.

SUMMARY

The invention relates to a method of creating a sensor that may include applying a first conductive material on a first portion of a substrate to form a reference electrode and depositing a first mask over the substrate, the first mask having an opening that exposes the reference electrode and a second portion of the substrate. The method may also include depositing a second conductive material into the opening in the first mask, the second conductive material being in direct contact with the reference electrode and depositing a second mask over the second conductive material, the second mask having an opening over the second portion of the substrate, the opening exposing a portion of the second conductive material, which forms a working surface to receive a fluid of interest.

The invention relates to a method of creating a sensor that may include applying a first conductive material on a first portion of a substrate to form a reference electrode and a second portion of the substrate to form a working electrode, and depositing a first mask on the substrate, the first mask having an opening that exposes the reference electrode, the working electrode, and an area between the reference electrode and the working electrode. The method may also include depositing a second conductive material on the reference electrode and in the area between the reference electrode and the working electrode and depositing a second mask on the second conductive material.

BRIEF DESCRIPTION OF THE DRAWINGS

The features, objects, and advantages of the invention will become more apparent from the detailed description set forth below when taken in conjunction with the drawings, wherein.

DETAILED DESCRIPTION

The invention is directed toward using a flex circuit to create a reference electrode channel. The flex circuit has a reference electrode that is masked and imaged onto a substrate. A first mask is deposited on the substrate. The first mask may have an opening that has a first end that exposes a portion of the reference electrode and a second end that exposes a portion of the substrate. The opening forms a reference electrode channel. A conductive material may be deposited into the opening of the first mask. A second mask is deposited on the first mask and the conductive material. The second mask may have an opening that exposes a portion of the conductive material that is over the substrate.

Figure 1:
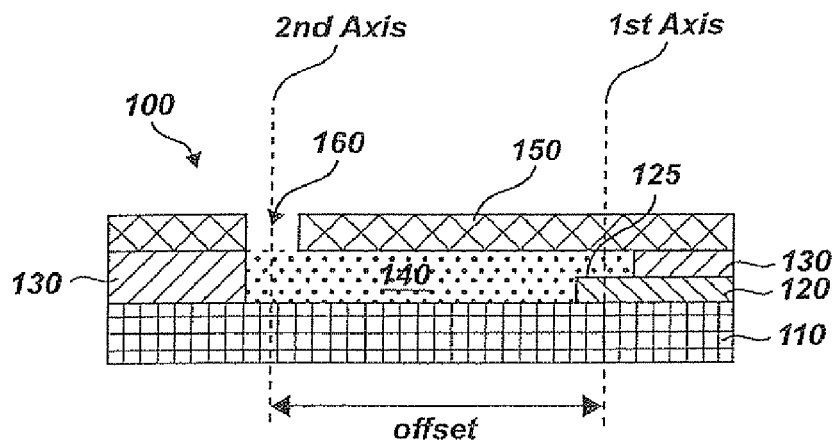
FIG. 1 is a cross-section view of a reference electrode channel that is created using a flex circuit according to an embodiment of the invention.

FIG. 1 is a cross-section view of a reference electrode channel that is created using a flex circuit according to an embodiment of the invention. The flex circuit 100 may include a substrate 110, a trace 120, and a reference electrode 125. The trace 120 and the reference electrode 125 may be masked and imaged onto the substrate 105. For example, the trace 120 and the reference electrode 125 may be formed on the substrate 105 using screen printing or ink deposition techniques. The trace 120 and the reference electrode 125 may be made of a carbon, copper, gold, graphite, platinum, silver-silver chloride, rhodium, or palladium material.

A first mask 130 may be applied or deposited over a portion of the substrate 110 and over the trace 120. The first mask 130 may have an opening 135 that expose a portion of the reference electrode 125 and a portion of the substrate 110. The opening 135 forms the reference electrode channel. A conductive material 140 is deposited in the opening 135 to cover the exposed portion of the reference electrode 125 and the exposed portion of the substrate 110. A second mask 150 may be applied or deposited over the first mask 130 and the conductive material 140. The second mask 150 may have an opening 160 over a portion of the conductive material 140 that is over the substrate 110. The opening 135 is positioned along a first axis or plane and the opening 160 is positioned along a second axis or plane. The first axis or plane is not coincident with the second axis or plane. Hence, the first axis or plane is vertically and/or horizontally offset from the second axis or plane.

The opening 160 is the measurement site and allows a fluid of interest (e.g., blood, urine, etc.) to come into contact with the conductive material 140 to complete the measurement circuit with another measuring electrode (not show) in contact with the same fluid. The conductive material 140 stabilizes the reference potential in several ways. The conductive material 140 may provide known silver and chloride ion activity, for example, (in the case of a silver-silver chloride reference design) to maintain a stable potential. The conductive material 140 should offer sufficient diffusion resistance to inhibit loss of desired ions to the fluid of interest, while simultaneously inhibiting migration of unwanted ions toward the active surface of the reference electrode 125. Spacing the opening 160 a sufficient distance from the reference electrode 125, as shown in FIG. 1, enhances this diffusion resistance. Finally, the conductive material 140 may provide a predictable junction potential at the interface with the fluid of interest which facilitates accurate electrochemical measurements using the reference electrode 125.

Figure 2:
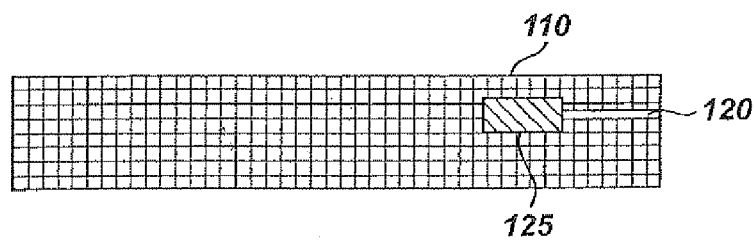
FIG. 2 is a top view of a flex circuit according to an embodiment of the invention.

FIG. 2 is a top view of a flex circuit 100 according to an embodiment of the invention. The trace 120 and the reference electrode 125 may be made of a conductive material such as a silver-silver chloride (Ag/AgCl) material and may be formed on the substrate 110 using photolithography or printing techniques (610). For example, the trace 120 and the reference electrode 125 may be formed on the substrate 110 using screen printing or ink deposition techniques. The substrate 110 may be a flexible dielectric substrate such as a polyimide. The trace 120 may be used to connect to a measurement device (not shown) such as a potentiostat. The trace 120 is used to measure a potential from the reference electrode 125 using the measurement device. Even though FIG. 1 shows the flex circuit 100 having one trace 120 and one reference electrode 125, the flex circuit 100 may have more than one trace and more than one electrode.

Figure 3:
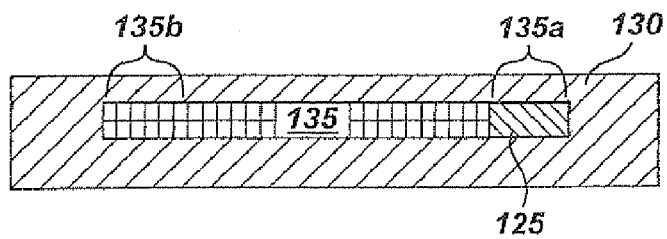
FIG. 3 is a top view of a mask that is used to cover the flex circuit shown in FIG. 2 according to an embodiment of the invention.

FIG. 3 is a top view of a mask 130 that is used to cover the flex circuit 100 shown in FIG. 2 according to an embodiment of the invention. The mask 130 may be made of a dielectric material such as a photoimagable epoxy or an ultraviolet curable epoxy material. The mask 130 is deposited over the substrate 110 and has a rectangular opening 135 that has a first end 135a that exposes a portion of the reference electrode 125 and a second end 135b that exposes a portion of the substrate 110 (620). The rectangular opening 135 may have a length of between about 0.10-0.20 inches and a width of between about 0.010-0.020 inches. The length-to-width ratio of the rectangular opening 135 may be in the range of between about 4:1 to 12:1. In one embodiment, the mask 130 covers the entire top surface of the flex circuit 100 except for the rectangular opening 135. The mask 130 may have a thickness of between about 0.005 inches and about 0.02 inches. The first end 135a of the opening 135 is positioned directly above the electrode 125 so that the electrode 125 is exposed or visible through the opening 135 of the mask 130. Lithography techniques may be used to deposit or place the mask 130 on the flex circuit 100.

Figure 4:
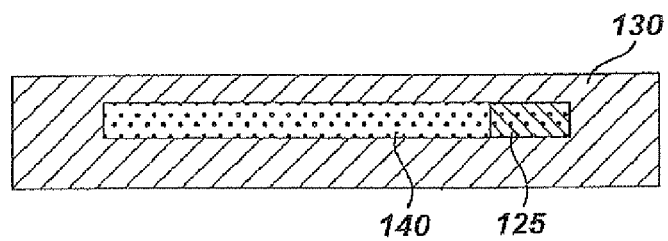
FIG. 4 is a top view showing a conductive material deposited into the opening of the mask according to an embodiment of the invention.

FIG. 4 is a top view showing a conductive material 140 deposited into the opening 135 of the mask 130 according to an embodiment of the invention. The conductive material 140 is deposited in the opening 135 to cover and to come into direct contact with the exposed portion of the reference electrode 125 and the exposed portion of the substrate 110 (630). The conductive material 140 may be a conductive fluid, a conductive solution, a conductive gel, a salt containing gel, a conductive polymer containing potassium chloride (KCl) with a small amount of silver ion ($Ag^+$), or a material having conductive properties. For the case of a silver-silver chloride reference electrode 125, addition of a trace of silver nitrate solution to a matrix containing potassium chloride precipitates some amount of silver chloride within the conductive matrix, but maintains a silver ion concentration at a constant amount according to the solubility product of silver chloride, which is $1.56 \times 10^{-10}$.

Figure 5:
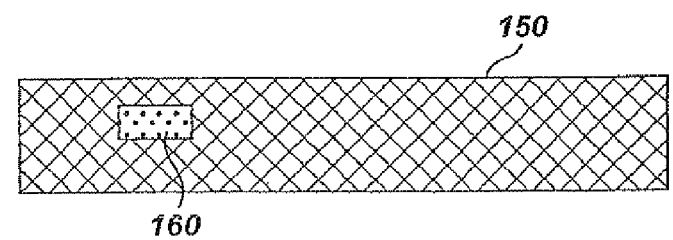
FIG. 5 is a top view of a mask that is used to cover a portion of the conductive material and the mask shown in FIG. 4 according to an embodiment of the invention.
Figure 6:
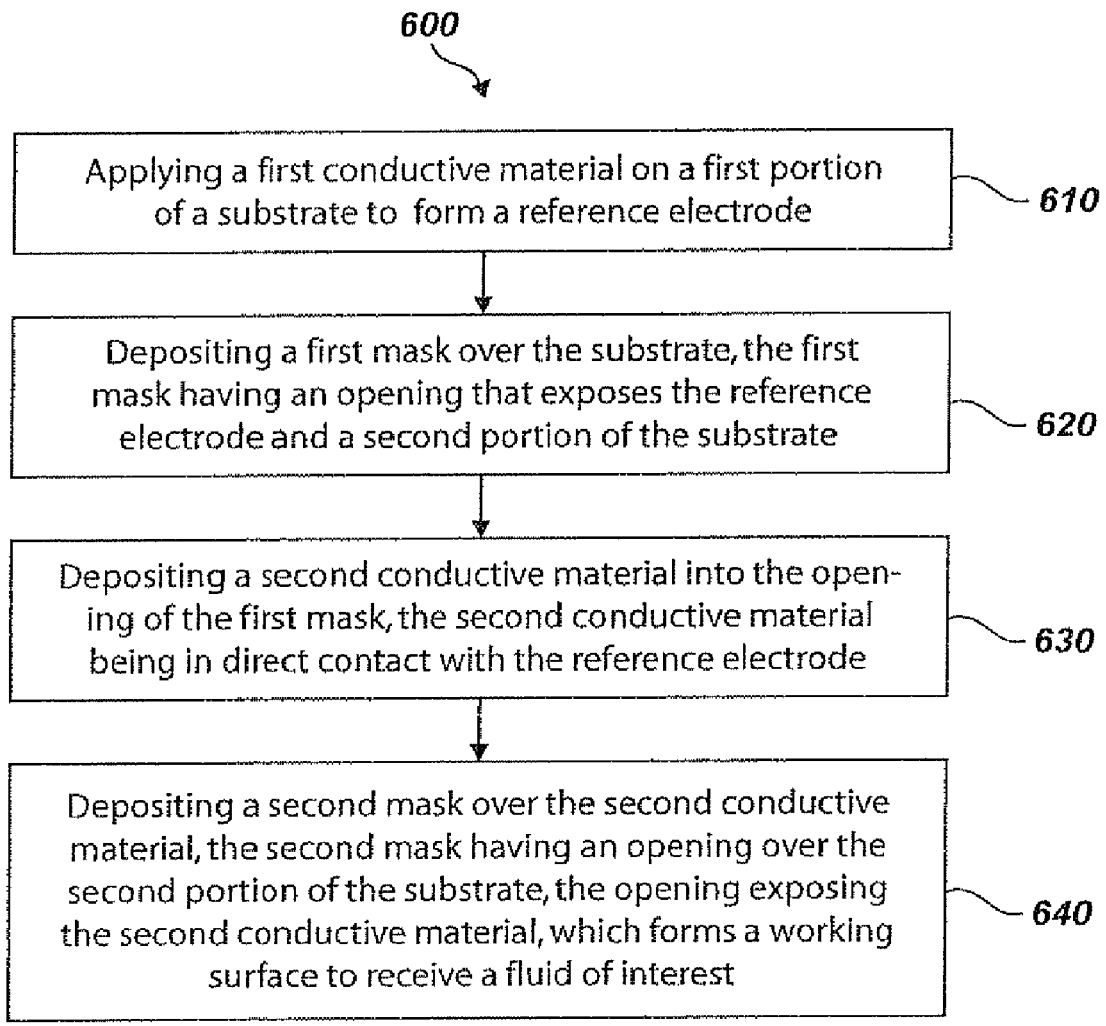
FIG. 6 is a flow chart showing a method of creating the reference electrode channel of FIG. 1 according to an embodiment of the invention.

FIG. 5 is a top view of a mask 150 that is used to cover a portion of the conductive material 140 and the mask 130 shown in FIG. 4 according to an embodiment of the invention. The mask 150 may be made of a dielectric material such as a photoimagable epoxy or an ultraviolet curable epoxy material. The mask 150 has an opening 160 that exposes a portion of the conductive material 140 that forms a working surface to receive a fluid of interest (640). Lithography techniques may be used to deposit or place the mask 150 on the mask 130 and the conductive material 140. FIG. 6 shows a flow chart of the method of creating the reference electrode channel corresponding to FIGS. 1-5 as described above.

Figure 7:
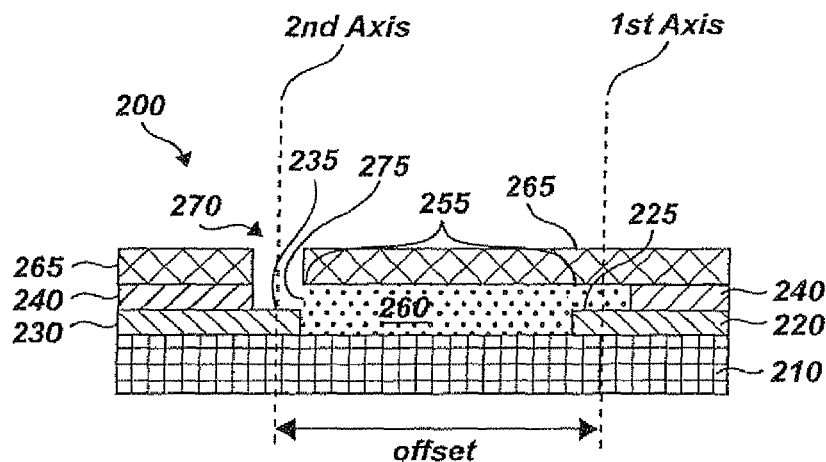
FIG. 7 is a cross-section view of a reference electrode channel that is created using a flex circuit according to an embodiment of the invention.

FIG. 7 is a cross-section view of a reference electrode channel that is created using a flex circuit according to an embodiment of the invention. The flex circuit 200 may include a substrate 210, traces 220 and 230, a reference electrode 225, and a working electrode 235. The traces 220 and 230, the reference electrode 225, and the working electrode 235 may be masked and imaged onto the substrate 210. For example, the traces 220 and 230, the reference electrode 225, and the working electrode 235 may be formed on the substrate 210 using screen printing or ink deposition techniques. The traces 220 and 230, the reference electrode 225, and the working electrode 235 may be made of a carbon, copper, gold, graphite, platinum, silver-silver chloride, rhodium, or palladium material.

A first mask 240 may be applied or deposited over a portion of the substrate 210 and over the traces 220 and 230. The first mask 240 may have an opening 250 that expose a portion of the reference electrode 225, a portion of the working electrode 235, and a portion of the substrate 210. The term "channel" (shown as channel 255) may be used to refer to the portion between the reference electrode 225 and the working electrode 235. Hence, the opening 250 may form the reference electrode channel. A conductive material 260 is deposited in the opening 250 to cover and to come into direct contact with the exposed portion of the reference electrode 225 and up to the edge of the exposed portion of the substrate 210. A second mask 265 may be applied or deposited over the first mask 240 and the conductive material 260. The second mask 265 may have an opening 270 over a portion of the working electrode 235. The reference electrode 225 is positioned along a first axis or plane and the working electrode 235 is positioned along a second axis or plane. The first axis or plane is not coincident with the second axis or plane. Hence, the first axis or plane is vertically and/or horizontally offset from the second axis or plane.

The opening 270 is the measurement site and allows a fluid of interest (e.g., blood, urine, etc.) to come into contact with the working electrode 235 and the conductive material 260 for a more accurate measurement. The conductive material 260 stabilizes the reference potential in several ways. The conductive material 260 may provide known silver and chloride ion activity for example (in the case of a silver-silver chloride reference design) to maintain a stable potential. The conductive material 260 should offer sufficient diffusion resistance to inhibit loss of desired ions to the solution, while simultaneously inhibiting migration of unwanted ions toward the active surface of the reference electrode 225. Spacing the opening 270 a sufficient distance from the reference electrode 225, as shown in FIG. 7, enhances this diffusion resistance. In addition, the opening 270 communicates directly with the end of the conductive material 260 at a smaller opening 275. The proximity of the smaller opening 275 to the working electrode 235 makes this embodiment ideal for situations where the solution resistance between the reference electrode and the working electrode needs to be keep at a minimum, such as in the case of a 3-electrode amperometric cell, for example.

Figure 8:
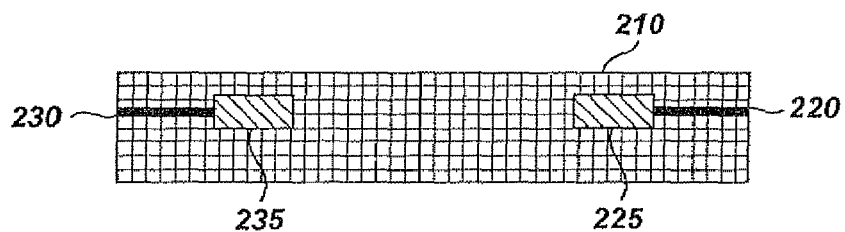
FIG. 8 is a top view of a flex circuit according to an embodiment of the invention.

FIG. 8 is a top view of a flex circuit 200 according to an embodiment of the invention. The traces 220 and 230, the reference electrode 225 and the working electrode 235 may be made of a conductive material such as a copper material, a platinum material, a silver-silver chloride (Ag/AgCl) material and are formed on the substrate 210 using masking and photolithography techniques (1210). For example, the traces 220 and 230, the reference electrode 225, and the working electrode 235 may be formed on the substrate 210 using screen printing or ink deposition techniques. The substrate 210 may be a flexible dielectric substrate such as a polyimide. The traces 220 and 230 may be used to connect to a measurement device (not shown) such as a potentiostat. The traces 220 and 230 may be used to carry voltage or current from the reference electrode 225 and the working electrode 235 to the measurement device.

Figure 9:
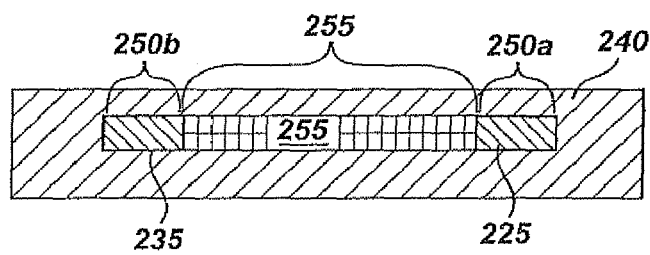
FIG. 9 is a top view of a mask that is used to cover the flex circuit shown in FIG. 8 according to an embodiment of the invention.

FIG. 9 is a top view of a mask 240 that is used to cover the flex circuit 200 shown in FIG. 8 according to an embodiment of the invention. The mask 240 may be made of a dielectric material such as a photoimagable epoxy or an ultraviolet curable epoxy material. The mask 240 is deposited over the substrate 210 and has a rectangular opening 250 that has a first end 250a that exposes a portion of the reference electrode 225, a second end 250b that exposes a portion of the working electrode 235, and a channel or an area 255 between the reference electrode 225 and the working electrode 235 that exposes a portion of the substrate 210 (1220). The rectangular opening 250 may have a length of between about 0.10-0.20 inches and a width of between about 0.010-0.020 inches. The length-to-width ratio of the rectangular opening 250 may be in the range of between about 4:1 to 12:1. In one embodiment, the mask 240 covers the entire top surface of the flex circuit 210 except for the rectangular opening 250. The mask 240 may have a thickness of between about 0.005 inches and about 0.02 inches. In one embodiment, the first end 250a of the opening 250 is positioned directly above the reference electrode 225 so that the reference electrode 225 is exposed or visible through the opening 250 of the mask 240. In one embodiment, the second end 250b of the opening 250 is positioned directly above the working electrode 235 so that the working electrode 235 is exposed or visible through the opening 250 of the mask 240. Lithography techniques may be used to deposit or place the mask 240 on the flex circuit 200.

Figure 10:
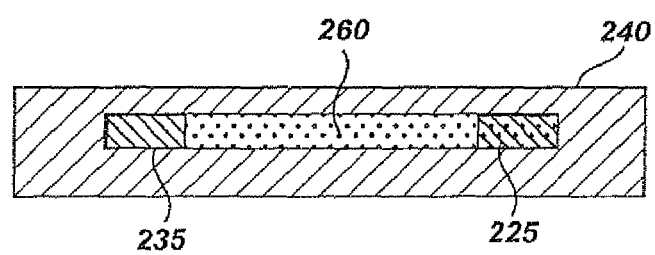
FIG. 10 is a top view showing a conductive material deposited into the opening of the mask according to an embodiment of the invention.

FIG. 10 is a top view showing a conductive material 260 deposited into the opening 250 of the mask 240 according to an embodiment of the invention. The conductive material 260 is deposited in the opening 250 to cover and to come into direct contact with the exposed portion of the reference electrode 225 and in the area 255 between the reference electrode 225 and the working electrode 235 (i.e., on the exposed portion of the substrate 210) (1230). In one embodiment, a screenable gel or a conductive polymer is applied in the opening 250 to cover and to come into direct contact with the exposed portion of the reference electrode 225 and in the area 255 between the reference electrode 225 and the working electrode 235. The conductive material 260 may be a conductive fluid, a conductive solution, a conductive gel, a salt containing gel, a conductive polymer containing potassium chloride (KCl) with a small amount of silver ion ($Ag^+$), or a material having conductive properties. The conductive material 260 may form a salt channel or a reference electrode channel.

Figure 11:
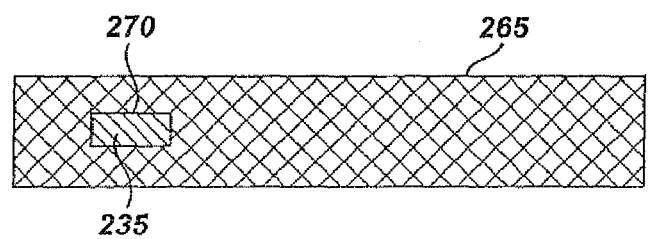
FIG. 11 is a top view of a mask that is used to cover the conductive material and the mask shown in FIG. 10 according to an embodiment of the invention.
Figure 12:
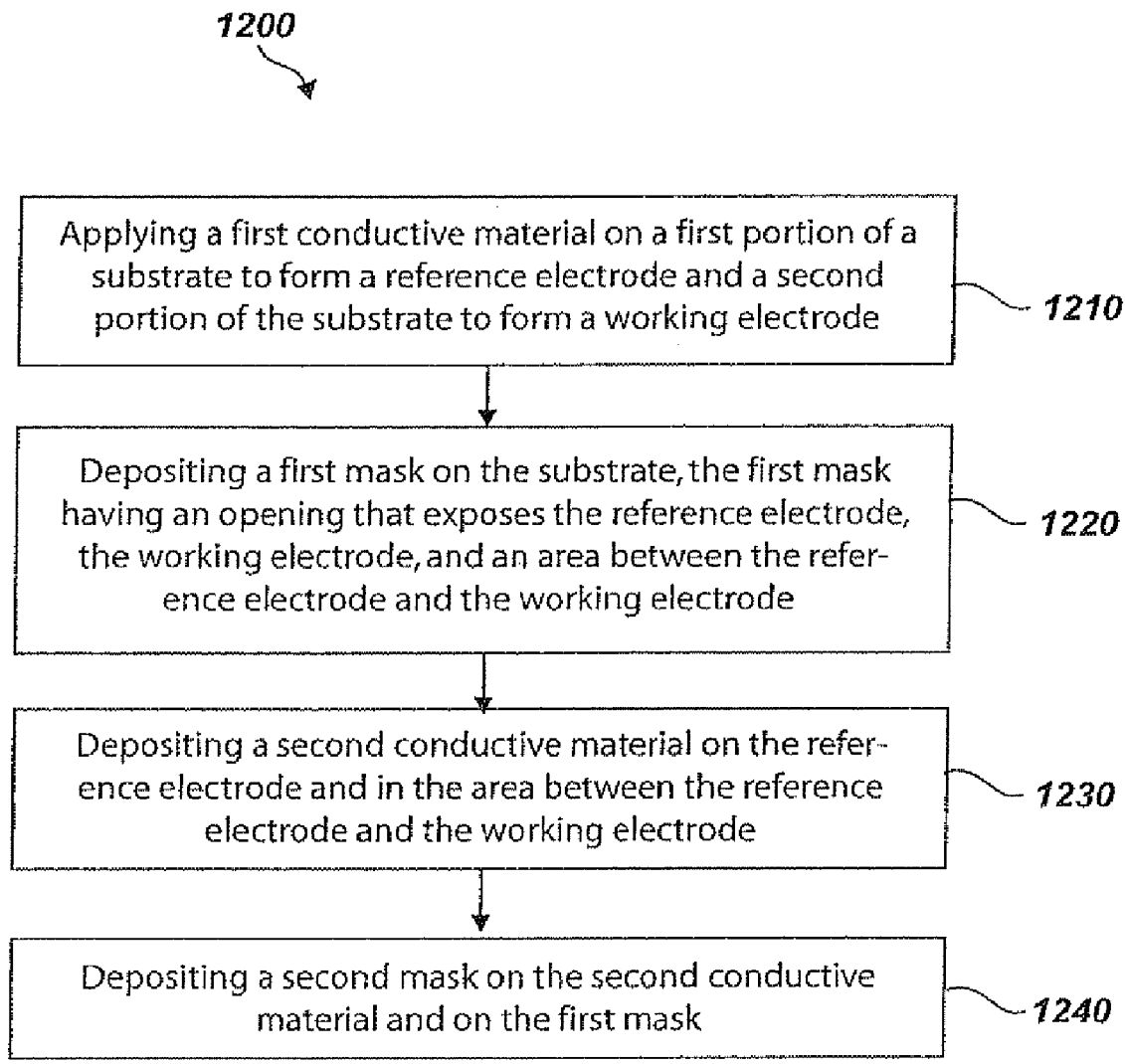
FIG. 12 is a flow chart showing a method of creating the reference electrode channel of FIG. 7 according to an embodiment of the invention.

FIG. 11 is a top view of a mask 265 that is used to cover the conductive material 260 and the mask 240 shown in FIG. 10 according to an embodiment of the invention. The mask 265 may be made of a dielectric material such as a photoimagable epoxy or an ultraviolet curable epoxy material. The mask 265 has an opening 270 that exposes a portion of the working electrode 235 and an edge of the conductive material 260, which forms a space to receive a fluid of interest. Lithography techniques may be used to deposit or place the mask 265 on the mask 240 and the conductive material 260 (1240). FIG. 12 shows a flow chart of the method of creating the reference electrode channel corresponding to FIGS. 7-11 as described above.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention. Therefore, it is to be understood that, within the scope of the appended claims, the invention may be practiced other than as specifically described herein.

What is claimed is:

1. A method of creating a sensor, the method comprising:
   applying a first conductive material on a first portion of a substrate to form a reference electrode;
   depositing a first mask over the substrate, the first mask having an opening that exposes the reference electrode and a second portion of the substrate;
   depositing a second conductive material into the opening in the first mask, the second conductive material being in direct contact with the reference electrode; and
   depositing a second mask over the second conductive material, the second mask having an opening over the second portion of the substrate, the opening exposing a portion of the second conductive material, which forms a working surface to receive a fluid of interest.

2. The method of claim 1, wherein the opening in the first mask is positioned along a first axis and the opening in the second mask is positioned along a second axis that is not coincident with the first axis.

3. The method of claim 2, wherein the first axis is horizontally offset from the second axis.

4. The method of claim 2, wherein the first axis is vertically offset from the second axis.

5. The method of claim 1, wherein the first conductive material is selected from a group consisting of a carbon, copper, gold, graphite, platinum, silver-silver chloride, rhodium, and palladium material.

6. The method of claim 1, wherein the second conductive material is selected from a group consisting of a conductive fluid, a conductive solution, a conductive gel, a salt containing gel, and a conductive polymer containing potassium chloride with a small amount of silver ion.

7. A method of creating a sensor, the method comprising:
applying a first conductive material on a first portion of a substrate to form a reference electrode and a second portion of the substrate to form a working electrode;
depositing a first mask on the substrate, the first mask having an opening that exposes the reference electrode, the working electrode, and an area between the reference electrode and the working electrode;
depositing a second conductive material on the reference electrode and in the area between the reference electrode and the working electrode; and
depositing a second mask on the second conductive material.

8. The method of claim 7, wherein the reference electrode is made of a silver-silver chloride material and the working electrode is made of a platinum material.

9. The method of claim 7, wherein the reference electrode is positioned along a first axis and the working electrode is positioned along a second axis that is not coincident with the first axis.

10. The method of claim 9, wherein the first axis is horizontally offset from the second axis.

11. The method of claim 9, wherein the first axis is vertically offset from the second axis.

12. The method of claim 7, wherein the first conductive material is selected from a group consisting of a carbon, copper, gold, graphite, platinum, silver-silver chloride, rhodium, and palladium material.

13. The method of claim 7, wherein the second conductive material is selected from a group consisting of a conductive fluid, a conductive solution, a conductive gel, a salt containing gel, and a conductive polymer containing potassium chloride with a small amount of silver ion.

* * * * *